United States Patent [19]

Hall et al.

[11] Patent Number: 5,068,088

[45] Date of Patent: Nov. 26, 1991

[54] METHOD AND APPARATUS FOR CONDUCTING ELECTROCHEMILUMINESCENT MEASUREMENTS

[75] Inventors: Lee O. Hall, Gaithersburg; Glenn Zoski, Rockville; Surendera K. Tyagi, Gaithersburg, all of Md.

[73] Assignee: Igen, Inc., Rockville, Md.

[21] Appl. No.: 325,459

[22] Filed: Mar. 17, 1989

Related U.S. Application Data

[63] Continuation-in-part of Ser. No. 267,234, Nov. 3, 1988.

[51] Int. Cl.$^5$ .................. G01N 21/76; H01J 1/62; H03K 4/00
[52] U.S. Cl. .................. 422/52; 250/361 C; 324/94; 328/178; 313/498
[58] Field of Search ............... 422/52; 315/169.3, 246; 313/498, 358, 505; 250/361 C; 340/781; 350/331 R, 332; 328/181, 178, 228, 261, 268, 186; 307/353; 204/231, 412, DIG. 9; 365/110, 111, 153; 324/94, 400, 153.1, 412

[56] References Cited

U.S. PATENT DOCUMENTS

| | | | |
|---|---|---|---|
| 3,816,795 | 6/1974 | Maricle et al. | 313/358 X |
| 3,868,534 | 2/1975 | Pighin et al. | 313/483 |
| 3,961,253 | 6/1976 | Brych | 324/94 |
| 4,204,037 | 5/1980 | Dill et al. | 435/3 |
| 4,236,895 | 12/1980 | Stahl | 422/52 X |
| 4,280,815 | 7/1981 | Oberhard et al. | 422/52 X |
| 4,303,410 | 12/1981 | Copeland | 250/361 C |
| 4,431,919 | 2/1984 | Kostlin et al. | 250/361 C |
| 4,443,713 | 4/1984 | Layton et al. | 307/261 |
| 4,591,733 | 5/1986 | Schröder | 307/246 |
| 4,721,601 | 1/1988 | Wrighton et al. | 422/68 |
| 4,771,215 | 9/1988 | Munakata et al. | 313/358 X |

FOREIGN PATENT DOCUMENTS

86/2734  5/1986  World Int. Prop. O. .
89/10551 11/1989  World Int. Prop. O. .

OTHER PUBLICATIONS

Y. Ikariyama, et al., Biochemical and Biophysical Research Comm., vol. 128, No. 2, pp. 987–992, 4/30/85.
Electrochemical Luminescence Based Homogeneous Immuno-Assay, Biochemical and Biophysical Research Communications, Ikariyama et al., vol. 128, No. 2, Apr. 1985, pp. 987–992.

*Primary Examiner*—Robert J. Warden
*Assistant Examiner*—Amalia L. Santiago
*Attorney, Agent, or Firm*—Curtis, Morris and Safford

[57] ABSTRACT

A method and apparatus for triggering and measuring electrochemiluminescent phenomena using a voltage waveform applied at the voltammetric working electrode which improves the precision and accuracy of measurements. This waveform has a decreasing scan rate in the range of voltages for which electrochemiluminescence is triggered and is substantially sinusoidal in shape in this range. The waveform results from locating the reference electrode of a potentiostat in close potential proximity to its counter electrode, and applying a uniform scanning voltage waveform at the reference electrode. The waveform also can be synthesized digitally, converted to analog form, and applied directly to the working electrode with the reference electrode in close potential proximity to the working electrode.

14 Claims, 3 Drawing Sheets

METHOD AND APPARATUS FOR CONDUCTING ELECTROCHEMILUMINESCENT MEASUREMENTS

This application is a continuation-in-part of U.S. patent application Ser. No. 267,234 filed Nov. 3, 1988, copending herewith.

FIELD OF THE INVENTION

This invention relates to electrochemiluminescent phenomena and more particularly to a system and method for detecting and measuring electrochemiluminescent phenomena.

BACKGROUND OF THE INVENTION

Measurement techniques for electrochemiluminescence (ECL) derive from electrochemistry (EC) and chemiluminescence (CL). EC deals generally with the relation of electricity to chemical changes and with the interconversion of chemical and electrical energy.

CL based assay or detection techniques generally comprise forming a mixture of a sample containing an unknown amount of an analyte of interest with a known amount of a reactant which is conjugated with a chemiluminescent label. The mixture is incubated to allow the labeled reactant to bind to the analyte and then is separated into a bound and an unbound fraction. One or both fractions are caused to luminesce by, for example, the addition of an oxidant to the fractions. The measured level of chemiluminescence at a specific wavelength is indicative of the amount of the bound or unbound fraction, and one skilled in the art can determine from such measurements the amount of analyte in the sample.

ECL detection techniques provide a sensitive and controllable measurement of the presence and amount of an analyte of interest In ECL, the incubated sample is exposed to a voltammetric working electrode, i.e., an electrode to which a voltage is applied and into which a current for a redox reaction is passed. The ECL mixture does not react with the chemical environment alone, as does the CL mixture, or with an electric field alone, as in EC, but rather electrochemiluminescence is triggered by a voltage impressed on the working electrode at a particular time and in a particular manner to controllably cause the ECL sample to emit light at the electrochemiluminescent wavelength of interest. The measurement is not the current at the electrode, as in EC, but the frequency and intensity of emitted light.

The operating conditions affecting an ECL measurement should be controlled from sample to sample before and during each measurement. A knowledge of these operating conditions is necessary to provide measurement results which are reproducible within useful limits. Because of the complexity of these conditions, however, and because the specific nature of all the chemical changes and reactions occurring during ECL is not completely known, there are substantial difficulties in reaching this goal.

Employees of the present assignee, under an obligation of assignment to it, have found that techniques which improve the measurement of current in EC do not necessarily improve the measurement of the frequency and intensity of light emitted during ECL. The optimal conditions for ECL measurements must meet different criteria.

The voltage waveform impressed upon the voltammetric electrode of an ECL cell must be sufficient to trigger electrochemiluminescence. This voltage waveform usually is in the form of a uniform voltage sweep starting at a first voltage, moving steadily to a second voltage, moving back through the first voltage to a third voltage and then back again to the first voltage. Other waveforms have been applied in practice, however, and can trigger ECL.

In order to be meaningful, the ECL measurement must be precise, i.e., repeatable within strict limits with the same operating conditions and ECL sample. The measurement also must be accurate, i.e., within acceptable limits of the actual concentration of analyte present in the sample. Since the ECL reaction chemically changes the sample, only one ECL measurement generally can be taken for each sample. These chemical changes occur predominantly within a thin layer of the sample adjacent the working electrode.

Precision and accuracy are sensitive to, among other things, the voltage waveform impressed upon the working electrode to trigger electrochemiluminescence. Although an optimal waveform may exist theoretically for a given sample and operating conditions, achieving this waveform is difficult because of the multiplicity of factors affecting the ECL response. The present inventors have found, however, that certain modifications in conventional waveforms, apparatus and techniques, which effectively diminish the extent to which this waveform is controlled at its operative point adjacent the working electrode, unexpectedly increase the quality of an ECL response and the precision and accuracy of its measurement.

OBJECTS AND SUMMARY OF THE INVENTION

It is an object of the present invention to provide a method and apparatus for improving the precision and accuracy of electrochemiluminescent measurements.

It is another object of this invention to provide a voltage waveform for triggering ECL which improves an ECL response and its measurement.

It also is an object of the present invention to provide a method and apparatus for impressing a voltage waveform on an ECL cell which enhances the precision and accuracy of ECL measurements.

It is a further object of the present invention to provide a method and apparatus for applying an improved waveform on an ECL cell using a potentiostat.

It is yet another object of the present invention to provide a method and apparatus for synthesizing a controlled voltage waveform for application to the working electrode of an ECL cell.

In accordance with one aspect of the present invention, the uniform scanning voltage waveform applied to the working electrode of an ECL cell to trigger electrochemiluminesence is modified such that the precision and accuracy of ECL measurements are improved. This modified waveform is substantially sinusoidal in shape at the voltages where ECL is triggered. This modification advantageously causes the ECL reaction to slow and occur more uniformaly and consistently and enables ECL measurements to be made more precisely and accurately.

A conventional electrochemical or ECL cell comprises a working electrode, a counter electrode and a reference electrode, and the voltage waveform for triggering electrochemiluminescence is applied to the working electrode using a potentiostat. The potentiostat applies a controlled voltage waveform at the reference electrode, with respect to the working electrode, and the working electrode is maintained at virtual ground. In order that the waveform adjacent the working electrode is known and controlled, the reference electrode is placed in close potential proximity to the working electrode.

In accordance with another aspect of this invention, the reference electrode of the ECL cell is placed in close potential proximity to the counter electrode, and a controlled voltage waveform is applied at the reference electrode. This placement diminishes the extent to which the waveform applied at the working electrode can be controlled. Because of the voltage drop within the cell between the counter and working electrodes, this waveform becomes modified at its operative point adjacent the working electrode. The amount of modification is substantially proportional to the resistance of the solution in the cell and the current passing between the counter and working electrodes. The present inventors have found that although the solution resistance remains substantially constant throughout an ECL event, the current in the cell increases near the voltage where light is emitted. As a result, if the controlled voltage waveform has a uniform scan rate, the waveform occurring at the working electrode decreases in scan rate and is found to become substantially sinusoidal in shape around the voltage at which ECL occurs. This modified waveform occurring at the working electrode, although subject to less control by the potentiostat, advantageously results in more precise and accurate ECL measurements.

This invention also comprises in another aspect synthesizing the modified waveform occurring at the working electrode, when the reference electrode is adjacent the counter electrode, and then applying this synthesized waveform directly to the working electrode with the reference electrode adjacent the working electrode for more precise control. With the reference electrode in the latter position, the operative waveform applied to the working electrode can be accurately controlled and closely monitored by the potentiostat.

Since the degree to which a waveform at the reference electrode becomes modified at the working electrode is substantially a function of the current flowing between the counter and working electrodes, this modified waveform can be calculated from a measure of the current flowing in the ECL cell during an ECL event. A computer or microprocessor can be used advantageously to perform this calculation and to synthesize the modified waveform digitally, and the digitally synthesized waveform can be converted to an analog waveform using an digital-to-analog converter. The synthesized analog waveform then can be applied precisely to the working electrode using a potentiostat with the reference electrode in close potential proximity to the working electrode. This method has the further advantage that small changes can be made to the synthesized waveform and accurately evaluated for further improvement in the ECL response and measurement.

In another aspect, this invention provides apparatus for applying a modified scanning voltage waveform to the working electrode of an ECL cell. This apparatus preferably comprises a potentiostat with its reference electrode in close potential proximity to its working electrode, and the modified waveform preferably is substantially a function of the current induced in the ECL cell during the triggering of electrochemiluminescence. Advantageously, the apparatus first synthesizes the modified waveform digitally, converts the digital waveform to an analog waveform and then applies the analog waveform to the working electrode using the potentiostat with its reference electrode in close potential proximity to the working electrode.

This invention also provides in another aspect a method for measuring electrochemiluminescent phenomena by applying a modified scanning voltage waveform to the working electrode of an ECL cell to trigger electrochemiluminesence with the modified voltage waveform being substantially a function of the current induced in the ECL cell during electrochemiluminescence. The modified voltage waveform preferably is the result of a uniform scanning voltage waveform (triangular waveform) minus a second waveform having a magnitude substantially a function of the current induced in the ECL cell.

Advantageously, this method further comprises synthesizing the modified voltage waveform digitally, converting the digital waveform to an analog waveform using an analog to digital converter and then applying the analog waveform to the working electrode of an ECL cell.

It is not intended that the invention be summarized here in its entirety. Rather, further features, aspects and advantages of the invention will be set forth in, or will be apparent from, the following description and drawings.

DETAILED DESCRIPTION OF THE PREFERRED EMBODIMENTS

Figure 1:
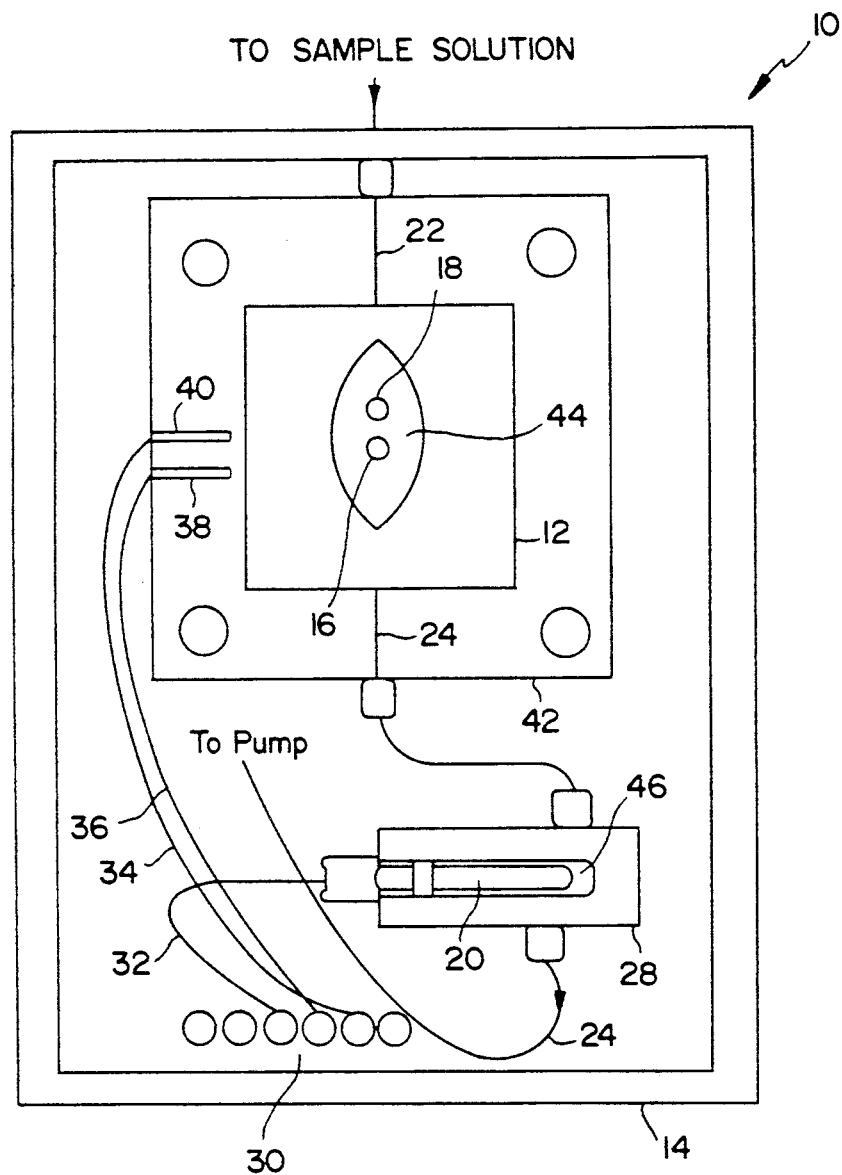
FIG. 1 is a front view of an apparatus according to the present invention.

FIG. 1 shows an ECL measuring apparatus 10 for applying the present invention. Apparatus 10 is a flow-through type ECL measuring apparatus, but, as is apparent from the following description, this invention is not limited to flow-through type ECL measuring apparatus and may be employed advantageously in all types of ECL apparatus utilizing a working electrode or other triggering surface to provide electrochemical energy to trigger an analyte of interest into electrochemiluminesence.

Apparatus 10 comprises an ECL cell 12, mounted on supporting structure 42, enclosed within light-tight drawer 14 which is removably mounted within a larger instrument for conducting ECL measurements. This instrument also includes detecting and measuring apparatus (not shown) for detecting and measuring the light emitted from a sample within the ECL cell 12 during ECL. The detecting and measuring apparatus advantageously may be a photomultiplier tube, photodiode, charge coupled device, photographic film or the like. For a further description of suitable detecting and measuring apparatus, reference is made to U.S. patent application Nos. 188,258 and 187,095, assigned in common with the present application.

Intake tubing 22, which may be constructed advantageously of stainless steel, passes through drawer 14 into a container (not shown) holding a solution to be sampled. A pump (also not shown), which is advantageously a peristaltic pump, at the end of exit tubing 24 causes a sample of this solution to pass through the intake tubing 22 into the sample holding volume 44 of the ECL cell. Electrochemiluminescence is triggered within the cell by working electrode 18 and counter electrode 16 and is measured by the detecting and measuring apparatus. After the measurement, the sample is pumped out of the holding volume 44, through exit tubing 24 (also advantageously constructed of stainless steel), and through the reference electrode holding volume 46. This process is repeated for each sample to be tested.

In order to substantially duplicate operating conditions prior to and during testing from sample to sample, various cleaning and conditioning solutions advantageously are pumped into the ECL cell prior to each sample. For a description of such cleaning and conditioning solutions and techniques for their application, reference is made to U.S. patent application No. 188,258, assigned in common with the present application.

Reference electrode 20 is incorporated within exit tubing 24 and enclosed within housing 28. In this position, this electrode is exposed to substantially the same voltage potential within the solution in sample holding volume 44 as that to which the counter electrode 16 is exposed. If housing 28 and reference electrode 20 were incorporated within the intake tubing 22, rather than the exit tubing 24, the reference electrode would be exposed to substantially the same voltage potential within the sample solution as that to which the working electrode 18 is exposed. The latter position is that generally used in a conventional electrochemical cell.

Figure 2:
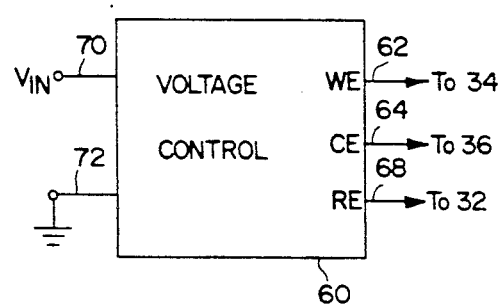
FIG. 2 is a block diagram of voltage control apparatus for controlling the voltages applied to the apparatus of FIG. 1.

Connectors 32, 34 and 36 connect the reference electrode 20, working electrode 18 and counter electrode 16, respectively, to terminal connectors 30 which are connected to the voltage control circuit 60 shown in FIG. 2. Male connectors 38 and 40 are removably inserted into female connectors within supporting structure 42 to enable the ECL cell to be electrically disassociated from the voltage control circuit and the working and counter electrodes to be reversed in function if desired.

Voltage control circuit 60, shown in FIG. 2, advantageously operates in the manner of a potentiostat to supply a controlled voltage waveform at reference electrode 20 with respect to the working electrode 18. Connectors 62, 64 and 68 of voltage control 60 are connected to terminals 30 and then to connectors 34, 36 and 32, respectively, which are connected to the working electrode 18, counter electrode 16 and reference electrode 20, respectively, of ECL apparatus 10. An input voltage $V_{in}$ to voltage control 60 is provided on connector 70. Connector 62, connected to the working electrode 18, and input connector 72 are held at virtual ground.

In operation, voltage control 60 forces the voltage appearing on connector 68, connected to the reference electrode 20, to duplicate $V_{in}$ appearing on input connector 70. No significant current flows through reference electrode 20, but this electrode provides a reference against which the voltage between the counter and working electrodes adjusts until the voltage at the reference electrode, with respect to the working electrode (i.e., ground), duplicates the voltage $V_{in}$ on connector 70. Potentiostats for this purpose are well known, and the internal structure of voltage control 60 may correspond to any of the conventional, commercially available potentiostats which operate in this manner.

Reference electrode 20 senses a voltage potential within the sample solution substantially equivalent to that adjacent counter electrode 16. If reference electrode 20 were located within the intake tubing 22 above the working electrode 18 shown in FIG. 1, then the reference electrode would sense substantially the same potential within the solution as that adjacent working electrode 18. The same result could be achieved by reversing male connectors 38 and 40 which would in effect make electrode 16 the working electrode and electrode 18 the counter electrode.

Locating the reference electrode at a voltage potential substantially equivalent to that adjacent the working electrode enables the voltage waveform applied to the working electrode to be precisely controlled and closely monitored. This position is conventional for electrochemical cells.

Figure 3:
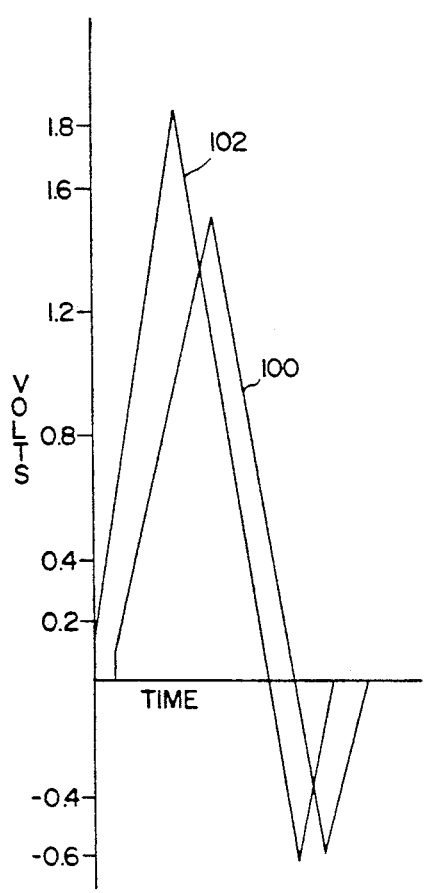
FIG. 3 is a waveform diagram illustrating voltages applied to the apparatus of FIG. 1.

FIG. 3 is a waveform diagram of voltages within ECL cell 12 during the triggering of ECL with the reference electrode 20 at a position for sensing the voltage substantially adjacent the working electrode (a position opposite to that shown in FIG. 1). Waveform 100 is the voltage applied at the reference electrode, and waveform 102 is the voltage measured within the solution by a probe substantially adjacent the counter electrode. The scan rate for the applied voltage 100 is 500 millivolts per second.

These plots show that voltage control 60, with the reference electrode and its conventional position for sensing the voltage adjacent the working electrode, forces both waveforms to be triangular and follow a substantially constant scan rate. At any given time, the voltage measured adjacent the counter electrode (waveform 102) exceeds that applied at the reference electrode (waveform 100) because of the voltage drop in the sample solution caused by the current between the working and counter electrodes. Electrochemicaluminescence is triggered at a point near the peak of both waveforms (approximately 1.4 volts applied at the reference electrode 20) without any modification or decrease in the scan rate during the period of ECL.

Figure 4:
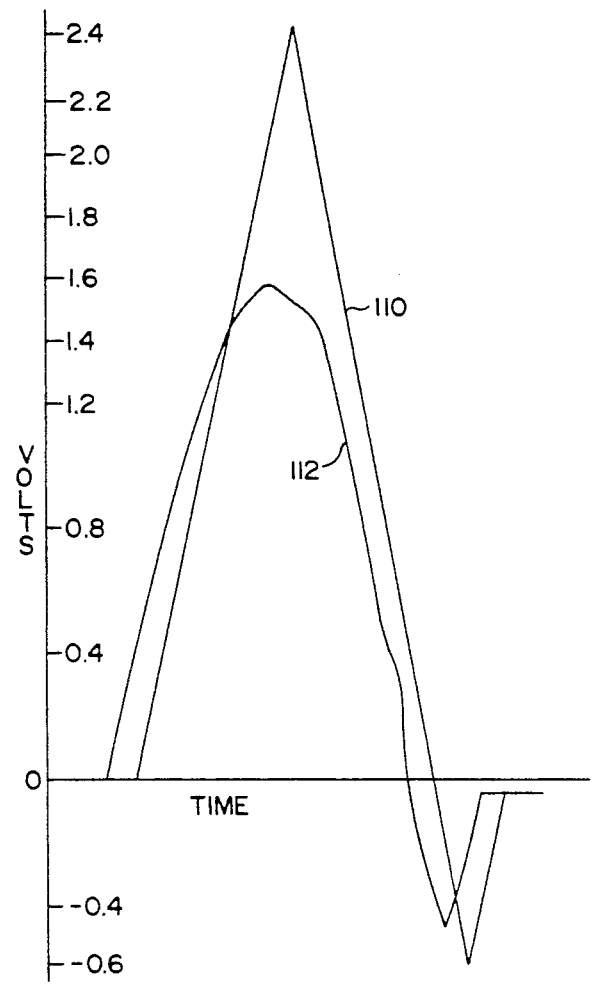
FIG. 4 is a waveform diagram illustrating voltages, modified in accordance with the present invention, for application to the apparatus of FIG. 1.

FIG. 4 is a waveform diagram of voltages within ECL cell 12 during the triggering of ECL with the reference electrode 20 in the alternative position shown in FIG. 1 for sensing the voltage adjacent the counter electrode. Waveform 110 is the voltage applied at the reference electrode, which has a uniform scan rate of 500 millivolts per second, and waveform 112 is the voltage measured within the sample solution by a probe substantially adjacent the working electrode. Waveform 112 shows a decrease in the scan rate or a plateauing around the period that electrochemiluminescence occurs. The voltage measured adjacent the working electrode during this period is between 1.4 and 1.6 volts. The potentiostat, however, keeps the applied voltage in the solution at the reference electrode adjacent the counter electrode, waveform 110, at the uniform, selected scan rate. The latter voltage exceeds the voltage adjacent the working electrode during chemiluminescence by approximately .8 volts because of the voltage drop between the counter and working electrodes resulting from the cascading of current during this period. This phenomenon keeps the voltage adjacent the working electrode at substantially that necessary to maintain electrochemiluminesce without overshooting this voltage and disadvantageously accelerating the event. This result enables a more precise and accurate electrochemiluminescent response and measurement of data.

Figure 5:
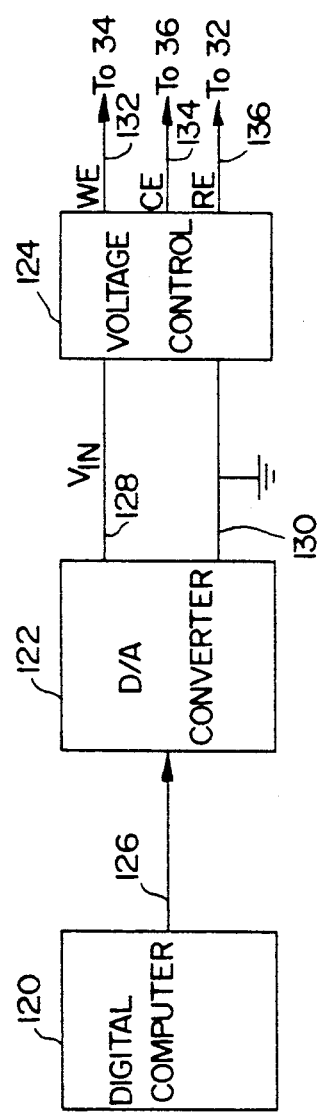
FIG. 5 is a block diagram of voltage control apparatus for synthesizing and applying the voltages illustrated in FIG. 4 to the apparatus of FIG. 1.

FIG. 5 shows a second embodiment of apparatus for control of the voltages applied to the apparatus of FIG. 1. This second embodiment advantageously synthesizes the waveform digitally that is applied at the reference electrode, with respect to the working electrode, using digital computer 120. This digitally synthesized waveform advantageously is equivalent to waveform 112, the waveform resulting at the working electrode with the reference electrode in its alternative position adjacent the counter electrode, when the waveform applied at the reference electrode is a uniform scanning voltage waveform. This synthesized waveform is applied to ECL cell 12 with reference electrode 20 in its conventional position adjacent working electrode 18. The digital synthesization of the waveform also can be effected with a microprocessor, special purpose computer or similar digital device.

Since the potential drop between the counter and working electrodes is primarily a function of the current flowing between these electrodes, the digitally synthesized waveform can be calculated from a measure of the current flowing in the ECL cell during ECL with the reference electrode in its alternative position adjacent the counter electrode. This current times the resistance of the sample solution defines a second waveform which is subtracted from the uniform scanning voltage waveform (triangular waveform) applied at the reference electrode to create the modified waveform.

The digitally synthesized waveform is fed through data lines 126 to digital to analog converter 122 whose output on connector 128, with respect to that appearing on connector 130 which is held at virtual ground, is the corresponding synthesized waveform in analog form. The voltage appearing on connector 128 is the input voltage $V_{in}$ to voltage control 124 which, like voltage control 60, advantageously operates in the manner of a potentiostat to supply a controlled voltage waveform substantially identical to $V_{in}$ on connector 136 with respect to connector 132 (virtual ground). In this embodiment, reference electrode 20 is located within the intake tubing 22 (opposite to the position shown in FIG. 1) for sensing the voltage potential within the sample solution substantially equivalent to that surrounding working electrode 18. Connectors 132, 134 and 136 of voltage control 124 are connected through terminals 30 to connectors 34, 36 and 32, respectively, and, therefore, to the working electrode 18, counter electrode 16 and reference electrode 20, respectively, of ECL apparatus 10.

In this embodiment, the applied scanning waveform is synthesized with its desirable plateau and substantially sinusoidial shape around the voltage for triggering ECL, and this waveform is precisely applied directly to the working electrode. This embodiment also enables minor modifications to be made in the synthesized waveform, and the degree to which they improve or adversely affect ECL response and measurements, to be directly correlated.

Although embodiments of the present invention have been described in detail herein with reference to the accompanying drawings, it is apparent that the invention is not limited to these embodiments and drawings and that various changes and modifications may be effected by one skilled in the art without departing from the spirit and scope of the invention as defined in the following claims.

We claim:

1. Apparatus for measuring electrochemiluminescent phenomena of a sample, comprising:
    (a) cell means for holding a sample;
    (b) voltage control means, including a working electrode, a counter electrode, and a reference electrode, said working electrode being located within said cell means so as to be exposable to said sample for triggering electrochemiluminescence therein, said reference electrode being located in potential proximity to said working electrode so as to sense the voltage substantially adjacent thereto, said voltage control means further including means synthesizing a controlled voltage waveform which is substantially a function of a current induced in said sample during the triggering of electrochemiluminescence, said voltage control means being coupled with said reference electrode to apply said controlled voltage waveform at the location of said reference electrode; and
    (c) radiation detection means for detecting electrochemiluminescent radiation from said sample.

2. An apparatus as in claim 1, wherein said means synthesizing a controlled voltage waveform comprises a digital computer for producing a control voltage waveform which is substantially a function of the current induced in said sample during the triggering of electrochemiluminescence; and a potentiostat having a connector coupled with said digital computer to receive said control voltage waveform and an output coupled with said working electrode; said potentiostat being operative under the control of said control voltage waveform means to apply said control voltage waveform to said working electrode.

3. An apparatus as in claim 1, wherein said reference electrode is incorporated within tubing through which the sample is pumped into the cell means.

4. An apparatus as in claim 1, wherein said voltage control means comprises a digital computer which is operative to synthesize a controlled voltage waveform which is substantially sinusoidal in shape in the voltage range for which electrochemiluminescence is triggered.

5. An apparatus as in claim 1, wherein said voltage control means comprises a digital computer which is operative to synthesize a controlled voltage waveform which is a uniformly increasing voltage waveform which becomes substantially flat within a portion of the voltage range for which electrochemiluminisence is triggered.

6. An apparatus as in claim 1, wherein said means for synthesizing a controlled voltage waveform comprises a digital computer for synthesizing said controlled voltage waveform in digital form, and means for converting said digital waveform to an analog waveform.

7. A method for measuring electrochemiluminescent phenomena of a sample, said method comprising the steps of:
    (a) introducing said sample into a cell having a working electrode located within said cell so as to be exposable to said sample;
    (b) applying a controlled voltage waveform to said working electrode to trigger electrochemiluminescence in said sample;

(c) generating said controlled voltage waveform substantially as a function of the current induced in said sample during the triggering of electrochemiluminescence; and (d) detecting electrochemiluminescent radiation from said sample.

8. A method as in claim 7, wherein the step of generating said controlled voltage waveform comprises synthesizing said controlled voltage waveform in digital form and converting said digital waveform to an analog waveform.

9. A method as in claim 7, wherein the step of generating said controlled voltage waveform comprises generating a controlled voltage waveform which is substantially sinusoidal in shape in the voltage range for which electrochemiluminescence is triggered.

10. A method as in claim 7, wherein the step of generating said controlled voltage waveform comprises generating a controlled voltage waveform which is a uniformly increasing voltage waveform which becomes substantially flat within a portion of the voltage range for which electrochemiluminescence is triggered 11. An apparatus for operating a working electrode in a cell adapted to trigger electrochemiluminescence in a sample, comprising:

(a) holding means for receiving and holding a sample;

(b) working electrode means positioned in said holding means to be exposed to said sample; and (c) voltage control means applying a voltage waveform to said working electrode means to trigger electrochemiluminescence in said sample, said waveform being substantially a function of a current induced in said sample during said triggering.

12. An apparatus as in claim 11, wherein said voltage control means comprises a digital computer for producing a control voltage waveform which is substantially a function of the current induced in said sample during the triggering of electrochemiluminescence; and a potentiostat having a connector coupled with said digital computer to receive said control voltage waveform and an output coupled with said working electrode; said potentiostat being operative under the control of said control voltage waveform means to apply said control voltage waveform to said working electrode.

13. An apparatus as in claim 11, further comprising a digital computer for synthesizing said voltage waveform in digital form, and means for converting said digital waveform to an analog waveform.

14. An apparatus as in claim 11, further comprising:

counter electrode means positioned in said holding means to be exposed to said sample for supplying current to said working electrode means; and reference electrode means positioned in said holding means to be exposed to said sample in potential proximity to said counter electrode means for sensing a voltage;

said voltage control means being coupled with said reference electrode means to adjustably apply a predetermined voltage waveformat the position thereof such that the voltage waveform at said working electrode means corresponds to a difference between said predetermined voltage waveform and a voltage difference resulting from the flow of current between said counter electrode and said working electrode.

* * * * *